US008956603B2

(12) United States Patent
Ladet et al.

(10) Patent No.: US 8,956,603 B2
(45) Date of Patent: Feb. 17, 2015

(54) AMPHIPHILIC COMPOUNDS AND SELF-ASSEMBLING COMPOSITIONS MADE THEREFROM

(75) Inventors: Sébastien Ladet, Lyons (FR); Philippe Gravagna, Irigny (FR)

(73) Assignee: Sofradim Production (FR)

( * ) Notice: Subject to any disclaimer, the term of this patent is extended or adjusted under 35 U.S.C. 154(b) by 285 days.

(21) Appl. No.: 13/202,376

(22) PCT Filed: Feb. 22, 2010

(86) PCT No.: PCT/IB2010/000573
§ 371 (c)(1),
(2), (4) Date: Nov. 3, 2011

(87) PCT Pub. No.: WO2010/095045
PCT Pub. Date: Aug. 26, 2010

(65) Prior Publication Data
US 2012/0052042 A1   Mar. 1, 2012

Related U.S. Application Data

(60) Provisional application No. 61/154,377, filed on Feb. 21, 2009.

(51) Int. Cl.
| | |
|---|---|
| *A61K 31/74* | (2006.01) |
| *A61K 47/48* | (2006.01) |
| *A61K 9/00* | (2006.01) |
| *A61F 13/00* | (2006.01) |
| *A61F 2/00* | (2006.01) |
| *A61K 47/34* | (2006.01) |
| *C08L 5/00* | (2006.01) |

(52) U.S. Cl.
CPC .. *A61K 47/34* (2013.01); *C08L 5/00* (2013.01)
USPC ......... 424/78.17; 424/400; 424/422; 424/423

(58) Field of Classification Search
None
See application file for complete search history.

(56) References Cited

U.S. PATENT DOCUMENTS

| | | |
|---|---|---|
| 3,767,085 A | 10/1973 | Cannon et al. |
| 4,326,532 A | 4/1982 | Hammar |
| 4,359,049 A | 11/1982 | Redl et al. |
| 4,464,321 A | 8/1984 | Pittalis et al. |
| 4,538,920 A | 9/1985 | Drake |
| 4,753,536 A | 6/1988 | Spehar et al. |
| 4,839,345 A | 6/1989 | Doi et al. |
| 4,857,403 A | 8/1989 | De Lucca et al. |
| 4,880,662 A | 11/1989 | Habrich et al. |
| 5,021,207 A | 6/1991 | De Lucca et al. |
| 5,372,585 A | 12/1994 | Tiefenbrun et al. |
| 5,455,308 A | 10/1995 | Bastiaansen |
| 5,562,946 A | 10/1996 | Fofonoff et al. |
| 5,578,662 A | 11/1996 | Bennett et al. |
| 5,582,955 A | 12/1996 | Keana et al. |
| 5,612,050 A | 3/1997 | Rowe et al. |
| 5,804,318 A | 9/1998 | Pinchuk et al. |
| 5,911,942 A | 6/1999 | Fofonoff et al. |
| 6,099,563 A | 8/2000 | Zhong |
| 6,107,365 A | 8/2000 | Bertozzi et al. |
| 6,107,453 A | 8/2000 | Zuccato et al. |
| 6,312,725 B1 | 11/2001 | Wallace et al. |
| 6,342,591 B1 | 1/2002 | Zamora et al. |
| 6,451,032 B1 | 9/2002 | Ory et al. |
| 6,534,611 B1 | 3/2003 | Darling et al. |
| 6,552,103 B1 | 4/2003 | Bertozzi et al. |
| 6,570,040 B2 | 5/2003 | Saxon et al. |
| 6,576,000 B2 | 6/2003 | Carrison |
| 6,624,245 B2 | 9/2003 | Wallace et al. |
| 6,881,766 B2 | 4/2005 | Hain |
| 6,958,212 B1 | 10/2005 | Hubbell et al. |
| 7,012,126 B2 | 3/2006 | Matsuda et al. |
| 7,105,629 B2 | 9/2006 | Matsuda et al. |
| 7,122,703 B2 | 10/2006 | Saxon et al. |
| 7,144,976 B2 | 12/2006 | Matsuda et al. |
| 7,172,877 B2 | 2/2007 | Ting |
| 7,247,692 B2 | 7/2007 | Laredo |
| 7,294,357 B2 | 11/2007 | Roby |
| 7,371,719 B2 | 5/2008 | Stupp et al. |
| 7,375,234 B2 | 5/2008 | Sharpless et al. |
| 7,560,588 B2 | 7/2009 | Breitenkamp et al. |
| 7,618,944 B2 | 11/2009 | Breitenkamp et al. |
| 7,638,558 B2 | 12/2009 | Breitenkamp et al. |
| 7,667,012 B2 | 2/2010 | Saxon et al. |
| 7,795,355 B2 | 9/2010 | Matyjaszewski et al. |
| 7,807,619 B2 | 10/2010 | Bertozzi et al. |
| 7,981,444 B2 | 7/2011 | Tomalia et al. |
| 7,985,424 B2 | 7/2011 | Tomalia et al. |
| 8,034,396 B2 | 10/2011 | Kapiamba et al. |
| 2002/0016003 A1 | 2/2002 | Saxon et al. |

(Continued)

FOREIGN PATENT DOCUMENTS

| | | |
|---|---|---|
| BE | 1008260 A6 | 2/1996 |
| EP | 0490854 B1 | 9/1996 |

(Continued)

OTHER PUBLICATIONS

Krout et al., Cellulose surface grafting with polycaprolactone by heterogenous click-chemistry, Sep. 16, 2008, European Polymer Journal, 44, pp. 4074-4081.*
Riva et al., Contribution of "Click Chemistry" to the synthesis of antimicrobial aliphatic copolyester. 2008, 49, pp. 2023-2028.*
Zhang et al., 2-Azido-2-deoxycellulose:Syntheis and 1,3-Dipolar Cycloaddition, 2008, Helv. Chim. Acta, 91, 608-617.*
Shi et al., The immobilization of Proteins on Biodegradable Polymer Fibers via click Chemistry, Biomaterials 29 (2008), 1118-1126.*
Q. Shi, et al., "The Immobilization of Proteins on Biodegradable Polymer Fibers via Click Chemistry", Biomaterials, 29, (2008), pp. 1118-1126.
Jérôme, et al., "Recent Advances in the Synthesis of Aliphatic Polyesters Ring-Opening Polymerization", Advanced Drug Delivery Reviews, 60, (2008), pp. 1056-1076.

(Continued)

*Primary Examiner* — Michael B Pallay

(57) ABSTRACT

The present disclosure relates to amphiphilic compounds, self assembling compositions formed from the amphiphilic compounds and methods of making such compositions.

10 Claims, 3 Drawing Sheets

(56) References Cited

U.S. PATENT DOCUMENTS

| | | |
|---|---|---|
| 2002/0161170 A1 | 10/2002 | Matsuda et al. |
| 2002/0169275 A1 | 11/2002 | Matsuda et al. |
| 2002/0173616 A1 | 11/2002 | Matsuda et al. |
| 2003/0100086 A1 | 5/2003 | Yao et al. |
| 2003/0135238 A1 | 7/2003 | Milbocker |
| 2003/0162903 A1 | 8/2003 | Day |
| 2003/0176335 A1 | 9/2003 | Zhang et al. |
| 2003/0199084 A1 | 10/2003 | Saxon et al. |
| 2003/0205454 A1 | 11/2003 | Hlavinka et al. |
| 2004/0170752 A1 | 9/2004 | Luthra et al. |
| 2004/0185053 A1 | 9/2004 | Govindan |
| 2004/0209317 A1 | 10/2004 | Ting |
| 2004/0249438 A1 | 12/2004 | Lefranc et al. |
| 2005/0032081 A1 | 2/2005 | Ju et al. |
| 2005/0038472 A1 | 2/2005 | Furst |
| 2005/0148032 A1 | 7/2005 | Saxon et al. |
| 2005/0222427 A1 | 10/2005 | Sharpless et al. |
| 2005/0233389 A1 | 10/2005 | Ting et al. |
| 2005/0244453 A1 | 11/2005 | Stucke et al. |
| 2006/0018948 A1 | 1/2006 | Guire et al. |
| 2006/0036022 A1 | 2/2006 | Callaghan et al. |
| 2006/0085033 A1 | 4/2006 | Criscuolo et al. |
| 2006/0108393 A1 | 5/2006 | Heinrich et al. |
| 2006/0110782 A1 | 5/2006 | Bertozzi et al. |
| 2006/0142404 A1 | 6/2006 | Berge et al. |
| 2006/0147963 A1 | 7/2006 | Barone et al. |
| 2006/0193865 A1 | 8/2006 | Govindan |
| 2006/0228300 A1 | 10/2006 | Chang et al. |
| 2006/0228357 A1 | 10/2006 | Chang et al. |
| 2006/0240092 A1 | 10/2006 | Breitenkamp et al. |
| 2006/0276658 A1 | 12/2006 | Saxon et al. |
| 2007/0020620 A1 | 1/2007 | Finn et al. |
| 2007/0037964 A1 | 2/2007 | Saxon et al. |
| 2007/0060658 A1 | 3/2007 | Diaz et al. |
| 2007/0077564 A1 | 4/2007 | Roitman et al. |
| 2007/0086942 A1 | 4/2007 | Chang et al. |
| 2007/0087001 A1 | 4/2007 | Taylor et al. |
| 2007/0099251 A1 | 5/2007 | Zhang et al. |
| 2007/0140966 A1 | 6/2007 | Chang et al. |
| 2007/0178133 A1 | 8/2007 | Rolland |
| 2007/0178448 A1 | 8/2007 | Tsao et al. |
| 2007/0190597 A1 | 8/2007 | Agnew et al. |
| 2007/0212267 A1 | 9/2007 | Organ et al. |
| 2007/0244265 A1 | 10/2007 | Matyjaszewski et al. |
| 2007/0244296 A1 | 10/2007 | Tomalia et al. |
| 2007/0249014 A1 | 10/2007 | Agnew et al. |
| 2007/0254006 A1 | 11/2007 | Loose et al. |
| 2007/0258889 A1 | 11/2007 | Douglas et al. |
| 2007/0269369 A1 | 11/2007 | Gegg et al. |
| 2007/0272122 A1 | 11/2007 | Lahann et al. |
| 2007/0275387 A1 | 11/2007 | Ju |
| 2007/0298006 A1 | 12/2007 | Tomalia et al. |
| 2008/0015138 A1 | 1/2008 | Hamilton et al. |
| 2008/0021486 A1 | 1/2008 | Oyola et al. |
| 2008/0035243 A1 | 2/2008 | Breitenkamp et al. |
| 2008/0038472 A1 | 2/2008 | Suzuki et al. |
| 2008/0045686 A1 | 2/2008 | Meagher et al. |
| 2008/0050731 A1 | 2/2008 | Agnew et al. |
| 2008/0051562 A1 | 2/2008 | Chaikof et al. |
| 2008/0103564 A1 | 5/2008 | Burkinshaw et al. |
| 2008/0121657 A1 | 5/2008 | Voegele et al. |
| 2008/0138317 A1 | 6/2008 | Fung |
| 2008/0160017 A1 | 7/2008 | Baker et al. |
| 2008/0166363 A1 | 7/2008 | Govindan et al. |
| 2008/0171067 A1 | 7/2008 | Govindan et al. |
| 2008/0187956 A1 | 8/2008 | Carrico et al. |
| 2008/0199736 A1 | 8/2008 | Gadeken et al. |
| 2008/0200628 A1 | 8/2008 | Gadeken et al. |
| 2008/0207913 A1 | 8/2008 | Breitenkamp et al. |
| 2008/0214436 A1 | 9/2008 | Yu et al. |
| 2008/0214801 A1 | 9/2008 | Saxon et al. |
| 2008/0214831 A1 | 9/2008 | Sharpless et al. |
| 2008/0221043 A1 | 9/2008 | Harth et al. |
| 2008/0241856 A1 | 10/2008 | Wong et al. |
| 2008/0241892 A1 | 10/2008 | Roitman et al. |
| 2008/0242171 A1 | 10/2008 | Huang et al. |
| 2008/0248126 A1 | 10/2008 | Cheng et al. |
| 2008/0267878 A1 | 10/2008 | Robillard et al. |
| 2008/0283572 A1 | 11/2008 | Boyden et al. |
| 2008/0311412 A1 | 12/2008 | Fokin et al. |
| 2008/0317861 A1 | 12/2008 | Guan |
| 2009/0012457 A1 | 1/2009 | Childers et al. |
| 2009/0018646 A1 | 1/2009 | Zhao |
| 2009/0027603 A1 | 1/2009 | Samulski et al. |
| 2009/0038701 A1 | 2/2009 | Delmotte |
| 2009/0053139 A1 | 2/2009 | Shi et al. |
| 2009/0054619 A1 | 2/2009 | Baker et al. |
| 2009/0061010 A1 | 3/2009 | Zale et al. |
| 2009/0069561 A1 | 3/2009 | Fokin et al. |
| 2009/0082224 A1 | 3/2009 | Haddleton et al. |
| 2009/0099108 A1 | 4/2009 | Jones |
| 2009/0124534 A1 | 5/2009 | Reineke et al. |
| 2009/0137424 A1 | 5/2009 | Tsao et al. |
| 2009/0181402 A1 | 7/2009 | Finn et al. |
| 2009/0182151 A1 | 7/2009 | Wu et al. |
| 2009/0202433 A1 | 8/2009 | Chang et al. |
| 2009/0203131 A1 | 8/2009 | Reineke et al. |
| 2009/0214755 A1 | 8/2009 | Armani et al. |
| 2009/0220607 A1 | 9/2009 | Kiser et al. |
| 2009/0240030 A1 | 9/2009 | Ju et al. |
| 2009/0247651 A1 | 10/2009 | Kapiamba et al. |
| 2009/0250588 A1 | 10/2009 | Robeson et al. |
| 2009/0253609 A1 | 10/2009 | Fleury et al. |
| 2009/0259016 A1 | 10/2009 | Johnson et al. |
| 2009/0263468 A1 | 10/2009 | McAnulty et al. |
| 2009/0269277 A1 | 10/2009 | Chang et al. |
| 2009/0281250 A1 | 11/2009 | DeSimone et al. |
| 2009/0297609 A1 | 12/2009 | Shoichet et al. |
| 2009/0306310 A1 | 12/2009 | Wu et al. |
| 2009/0311425 A1 | 12/2009 | Tsubaki et al. |
| 2009/0312363 A1 | 12/2009 | Bradner et al. |
| 2009/0325292 A1 | 12/2009 | Baker et al. |
| 2010/0011472 A1 | 1/2010 | Hugel et al. |
| 2010/0015046 A1 | 1/2010 | Govindan et al. |
| 2010/0021391 A1 | 1/2010 | Douglas et al. |
| 2010/0034862 A1 | 2/2010 | Laronde et al. |
| 2010/0047258 A1 | 2/2010 | Wang et al. |
| 2010/0048738 A1 | 2/2010 | Fleury et al. |
| 2010/0069578 A1 | 3/2010 | Faust et al. |
| 2010/0098640 A1 | 4/2010 | Cohen et al. |
| 2010/0104589 A1 | 4/2010 | Govindan et al. |
| 2010/0121022 A1 | 5/2010 | Musa et al. |
| 2010/0159508 A1 | 6/2010 | Yang et al. |
| 2010/0247433 A1 | 9/2010 | Tirrell et al. |
| 2010/0286405 A1 | 11/2010 | Fokin et al. |
| 2010/0291171 A1 | 11/2010 | Crescenzi et al. |
| 2010/0303754 A1 | 12/2010 | Turpin et al. |
| 2011/0008251 A1 | 1/2011 | Chang et al. |
| 2011/0052696 A1 | 3/2011 | Hult et al. |
| 2011/0060107 A1 | 3/2011 | Matyjaszewski et al. |
| 2011/0143435 A1 | 6/2011 | Stayton et al. |
| 2011/0177156 A1 | 7/2011 | Szoka, Jr. et al. |
| 2011/0183417 A1 | 7/2011 | Reineke |
| 2011/0213123 A1 | 9/2011 | Bertozzi et al. |

FOREIGN PATENT DOCUMENTS

| | | |
|---|---|---|
| EP | 1790702 A1 | 5/2007 |
| EP | 1795563 A1 | 6/2007 |
| EP | 1975230 A1 | 1/2008 |
| EP | 2014308 A2 | 1/2009 |
| EP | 2090592 A1 | 8/2009 |
| WO | WO 03/070749 A2 | 8/2003 |
| WO | WO 2006/012569 A1 | 2/2006 |
| WO | WO 2006/034128 A2 | 3/2006 |
| WO | WO 2006034128 * | 3/2006 |
| WO | WO2006034128 * | 3/2006 |
| WO | WO 2007/041394 A2 | 4/2007 |
| WO | WO 2007/121055 A1 | 10/2007 |
| WO | WO 2008/013618 A1 | 1/2008 |
| WO | WO 2008/075955 A2 | 6/2008 |
| WO | WO 2008/077406 A2 | 7/2008 |
| WO | WO 2008/108736 A1 | 9/2008 |
| WO | WO 2008/115694 A2 | 9/2008 |

(56) References Cited

FOREIGN PATENT DOCUMENTS

| WO | WO 2008/120016 A1 | 10/2008 |
| WO | WO 2008/134734 A2 | 11/2008 |
| WO | WO 2010/095049 A1 | 8/2010 |

OTHER PUBLICATIONS

Zhang, et al., "2-Azido-2-deoxycellulose: Synthesis and 1,3-Dipolar Cycloaddition", Helvetica Chimica Acta, vol. 91, pp. 608-617 (2008).
Riva, et al., "Contribution of "Click Chemistry" to the Synthesis of Antimicrobial Aliphatic Copolyester", Polymer 49, (2008), pp. 2023-2028.
Baskin, et al., "Copper Free Click Chemistry for Dynamic In Vivo Imaging", PNAS, vol. 104, No. 43, (Oct. 23, 2007), pp. 16793-16797.
Codelli, et al., "Second Generation Difluorinated Cyclooctynes for Copper-Free Click Chemistry", J. Am. Chem. Soc., vol. 130, No. 34, (2008), pp. 11486-11493.
Sletten and Bertozzi, "A Hydrophilic Azacyclooctyne for Cu-free Click Chemistry", Org. Lett. (2008) 10(14), pp. 3097-3099.
Cazalis, et al., "C-Terminal Site-Specific PEGylation of a Truncated Thrombomodulin Mutant with Retention of Full Bioactivity", Bioconjugate Chem., (2004), 15, pp. 1005-1009.
Haridas, et al., "Design and Synthesis of Triazole-based Peptidedendrimers" Tetrahedron Letters, vol. 48, (2007), pp. 4719-4722.
Raghavan, et al., "Chemical Probes for Profiling Fatty Acid-associated Proteins in Living Cells", Bioorg. Med. Chem. Lett., 18 (2008), pp. 5982-5986.
LeDévédec, et al., "Separation of Chitosan Oligomers by Immobilized Metal Affinity Chromatography", Journal of Chromatography A, 2008, 1194(2), pp. 165-171.
Hartgerink, et al., "Peptide-amphiphile Nanofibers: A Versatile Scaffold for the Preparation of Self Assembling Materials", PNAS, 2002; 99(2), pp. 5133-5138.
Van Berkel, et al., "Metal-Free Triazole Formation as a Tool for Bioconjugation" Chem Bio Chem, 8, (2007), pp. 1504-1508.
Nottelet, et al., Synthesis of an X-ray opaque biodegradable copolyester by chemical modification of poly (ε-caprolactone) Biomaterials, 27, (2006), pp. 4943-4954.
Smith, et al., "Synthesis and Convenient Functionalization of Azide-labeled Diacyglycerol Analogues for Modular Access to Biologically Active Lipid Probes", Bioconjugate Chem, 19(9), (2008). pp. 1855-1863.
Skierka, et al., "The Influence of Different Acids and Pepsin on the Extractability of Collagen From the Skin of Baltic Cod (*Gadus morhua*)", Food Chemisty, 105, (2007), pp. 1302-1306.
Eastoe, "The Amino Acid Composition of Mammalian Collagen and Gelatin", vol. 61, (1955), pp. 589-600.
Sicherl, et al., "Orthogonally Protected Sugar Diamino Acids as Building Blocks for Linear and Branched Oligosaccharide Mimetics", Angew. Chem. Int. Ed. 44, (2005), pp. 2096-2099.
Laughlin, et al., "In Vivo Imaging of Membrane-Associated Glycans in Developing Zebrafish", Science, 320, (2008), pp. 664-667.
Worch and Wittmann, "Unexpected Formation of Complex Bridged Tetrazoles via Intramolecular 1,3-dipolar Cycloaddition of 1,2-0-cyanoalkylidene Derivatives of 3-azido-3-deoxy-D-allose", Carbohydrate Research, 343, (2008), pp. 2118-2129.
Witczak et al., "A Click Chemistry Approach to Glycomimetics: Michael addition of 2,3,4,6-tetra-O-acetyl-1-thio-β-D-glucopyranose to 4-deoxy-1,2-O-isopropylident-L-*glycero*-pent-4-enopyranos-3-ulose—a convenient route to novel 4-deoxy-(1→5)-5-C-thiodisaccharides", Carbohydrate Research, 342, (2007), 1929-1933.
Marra, et al., "Validation of the Copper(1)-Catalyzed Azide-Alkyne Coupling in Ionic Liquids, Synthesis of a Triazole-Linked C-Disaccharide as a Case Study", J. Org. Chem (2008), 73(6), pp. 2458-2461.
Srinivasachari, et al., "Versatile Supramolecular pDNA Vehicles via "Click Polymerization" of β-cyclodextrin with oligoethyleneamines", Biomaterials, 30, (2009), pp. 928-938.
Arora, et al., "A Novel domino-click approach for the synthesis of sugar based unsymmetrical bis-1,2,3-triazoles", Carbohydrate Research, 343, (2008), 139-144.
Chen, et al., "Synthesis of a $C_3$-symmetric (1→6)-N-acetyl-β-D-glucosamine Octadecasaccharide using Click Chemistry", Carbohydrate Research, 340, (2005), pp. 2476-2482.
Gouin, et al., "Multi-Mannosides Based on a Carbohydrate Scaffold: Synthesis, Force Field Development, Molecular Dynamics Studies, and Binding Affinities for Lectin Con A", J. Org. Chem., 2007, 72(24), pp. 9032-9045.
Srinivasachari, et al., "Effects of Trehalose Click Polymer Length on pDNA Complex Stability and Delivery Efficacy", Biomaterials, 28, (2007), pp. 2885-2898.
Godeau, et al., Lipid-Conjugated Oligonucleotides via "Click Chemistry" Efficiently Inhibit Hepatitis C Virus Translation, J. med. Chem., 2008, 51(15), pp. 2374-4376.
Zou et al., "Cu-free Cycloaddition for Identifying Catalytic Active Adenylation Domains of Nonribosomal Peptide Synthesis by phage display", Bioorganic & Medicinal Chemistry Letters, 18 (2008), pp. 5664-5667.
Cantel, et al., "Synthesis and Conformational Analysis of a Cyclic Peptide Obtained via $i$ to $i$+4 Intramolecular Side-chain to Side-chain Azide-Alkyne 1,3-Dipolar Cycloaddition" J. Org. Chem., 2008, 73 (15), pp. 5663-5614.
Dijk, et al., "Synthesis of Peptide-Based Polymers by Microwave-Assisted Cycloaddition Backbone Polymerization," Biomacro molecules, 2007, 8(2), pp. 327-330.
Köster, et al., "Spectroscopic and Electrochemical Studies of Ferroceryl Triazole Amino Acid and Peptide Bioconjugates Synthesized by Click Chemistry", Organometallics, 2008, 27(23) pp. 6326-6332.
Dijk, et al., "Synthesis and Characterization of Biodegradable Peptide-Baed Polymers Prepared by Microwave-Assisted Click Chemisty", Biomacromolecules, 2008, 9(10), pp. 2834-2843.
Jiang, et al., "Amphiphilic PEG/alkyl-grafted comb polylactides", J. Polymer Science Part B: Polymer Physics, 45(22), 2007, pp. 5227-5236.
Ochs, et al., "Low-Fouling, Biofunctionalized, and Biodegradable Click Capsules", Biomacromolecules, 2008, 9(12), pp. 3389-3396.
Beatty and Tirrell, "Two-color Labeling of Temporally Defined Protein Populations in Mammalian Cells", Bioorg. Med. Chem. Lett., 18 (2008), pp. 5995-5999.
Kolb, et al., "Click Chemistry: Diverse Chemical Function from a Few Good Reactions", Angewandte Chemie, International Edition, Jun. 2001, pp. 2004-2021.
Krouit, et al., "Cellulose surface grafting with polycaprolactone by heterogeneous click-chemistry", European Polymer Journal 44, Dec. 2008, pp. 4074-4081.
Nandivada, et al. "Reactive polymer coatings that 'Click'.", Angewandte Chemie, International Edition 45, Apr. 2006, pp. 3360-3363.
Ossipov and Hilborn, Poly(vinyl alcohol)-Based Hydrogels Formed by "Click Chemistry", Macromelecules 2006, 39, pp. 1709-1718.
Binder and Sachsenhofer, "Click Chemistry in Polymer and Materials Science", Macromolecular Rapid Commun. 2007, 28, pp. 15-54.
International Search Report for PCT/IB2010/000573 date of completion is Jun. 29, 2010 (3 pages).

\* cited by examiner

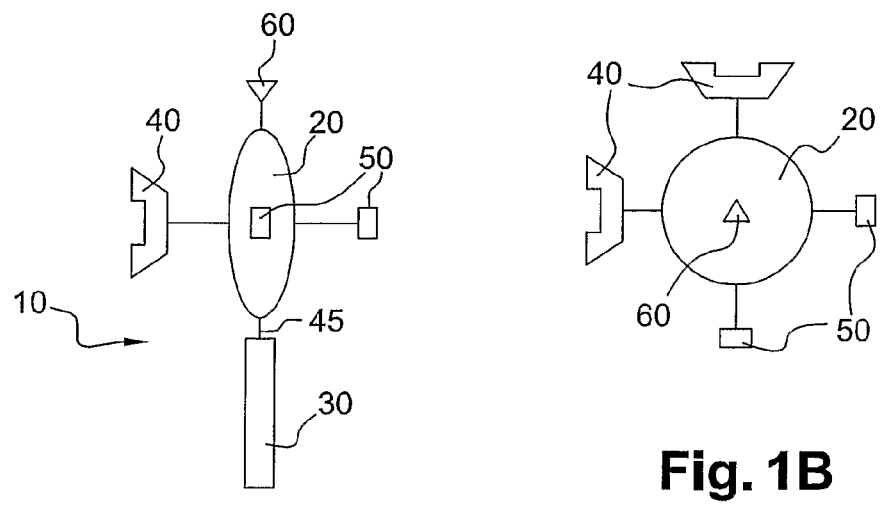
Fig. 1A
Fig. 1B
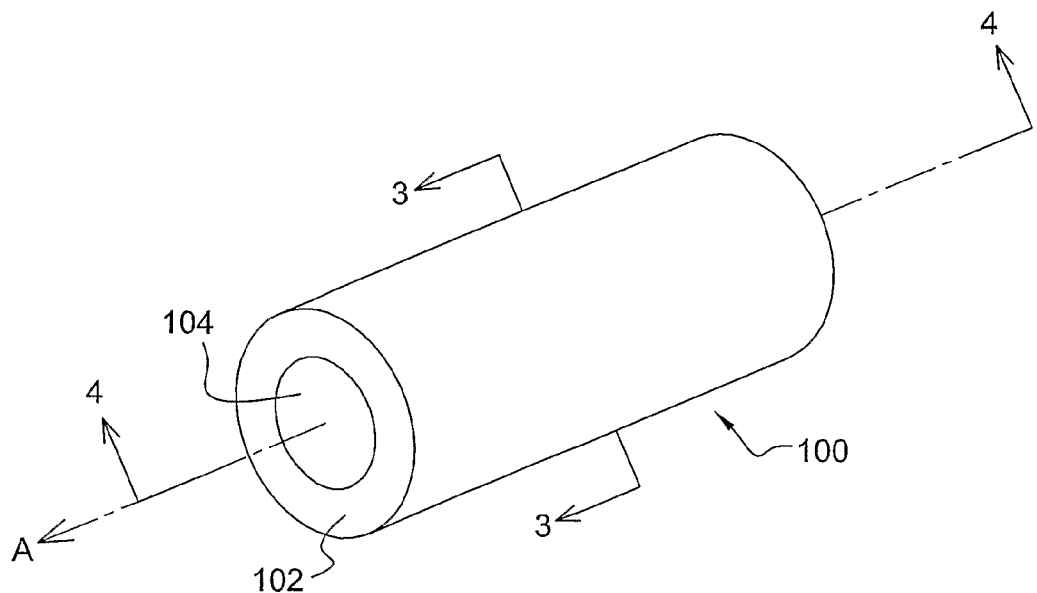
Fig. 2

AMPHIPHILIC COMPOUNDS AND SELF-ASSEMBLING COMPOSITIONS MADE THEREFROM

CROSS-REFERENCE TO RELATED APPLICATIONS

This application is a U.S. National Stage Application filed under 35 U.S.C. §371(a) of International Application No. PCT/IB2010/000573 filed Feb. 22, 2010, which claims the benefit of and priority to U.S. Provisional Application Ser. No. 61/154,377 filed Feb. 21, 2009, the entire contents of which are incorporated by reference herein.

BACKGROUND

1. Technical Field

The present disclosure relates to functionalized amphiphilic compounds and methods of making self assembling compositions therefrom.

2. Background of Related Art

Amphiphilic polymers, having a large solubility difference between hydrophilic and hydrophobic portions, are known to self-assemble in a variety of solutions into micelles of nanoscale size. Such micelles have a fairly narrow size distribution and are characterized by their unique core-shell architecture, where in a hydrophilic solution the hydrophobic portions are segregated from the aqueous exterior to form an inner core surrounded by a shell of hydrophilic polymer chains. A micelle is thermodynamically stable relative to disassembly into single chains as long as the concentration of the amphiphilic polymer exceeds the critical micelle concentration.

The principles of self-assembly of polymer micelles have been advanced by using block and graft (linear polymers to which side chains have been "grafted") copolymers containing ionic and nonionic blocks. Polymer micelles formed from block or graft copolymers are of interest because they allow the encapsulation of therapeutic molecules including pharmaceuticals, proteins, nucleic acids and other bioactive agents. Moreover, the architecture of the polymer micelles may be useful in the formation of structurally supportive nanofibers.

It would be beneficial to provide compositions that produce self-assembled structures with added stability against the environment in vivo by creating linkages between the amphiphilic compounds used to form the self-assembling structures.

SUMMARY

A first aspect of the invention is an amphiphilic compound comprising
   a hydrophilic portion and a hydrophobic portion, and
   at least two reactive members selected from the group consisting in first reactive members and second reactive members where the second reactive members are complementary to the first reactive members in that the first and second reactive members are able to interact with one another to form covalent bonds between each other,
   said at least two reactive members being both located on one of said hydrophilic portion and hydrophobic portion.

In embodiments, the first reactive members are electrophilic functional groups and the second reactive members are nucleophilic functional groups.

In other embodiments, the first reactive members include alkyne groups and the second reactive members include azide groups.

In other embodiments, the first reactive members include azide groups and the second reactive members include alkene groups.

In embodiments, the two reactive members are a first reactive member and a second reactive member. The two reactive members may be located on the hydrophilic portion. Alternatively, the two reactive members may be located on the hydrophobic portion.

In other embodiments, the two reactive members are two first reactive members. In such embodiments, the two first reactive members may be located on the hydrophilic portion. In embodiments the hydrophiphilic portion includes a plurality of first reactive members.

In the present application, by "plurality" is meant two or more.

In other embodiments, the two reactive members are two second reactive members. For example, the two reactive members are located on the hydrophilic portion. In embodiments, the hydrophilic portion includes a plurality of second reactive members.

In embodiments, the amphiphilic compound further comprises a terminal reactive member on the hydrophilic portion.

A further aspect of the invention is a composition comprising
   a hydrophilic solvent;
   optionally a catalyst;
   at least a first amphiphilic compound, said first amphiphilic compound being an amphiphilic compound as described above wherein the hydrophiphilic portion includes a plurality of first reactive members, and
   at least a second amphiphilic compound, said second amphiphilic compound being an amphiphilic compound as described above, wherein the hydrophilic portion includes a plurality of second reactive members. The invention relates also to a self assembled structure comprising
   at least a first amphiphilic compound, said first amphiphilic compound being an amphiphilic compound as described above wherein the hydrophiphilic portion includes a plurality of first reactive members, and
   at least a second amphiphilic compound, said second amphiphilic compound being an amphiphilic compound as described above wherein the hydrophilic portion includes a plurality of second reactive members,
   wherein one of the first reactive members of a first amphiphilic compound interact with one of the second reactive members of a second amphiphilic compound to covalently bond the hydrophilic portion of said first amphiphilic compound to the hydrophilic portion of said second amphiphilic compound. The invention also relates to a method of locking such a self assembled structure comprising:
   providing a composition as described above,
   reacting one of the first reactive member of a first amphiphilic compound with one of the second reactive member of a second amphiphilic compound.

Another aspect of the invention is a composition comprising a hydrophilic solvent and a plurality of amphiphilic compounds, the hydrophilic portion of includes a first reactive member and a second reactive member. The invention further relates to a self assembled structure comprising two or more amphiphilic compounds as described above, wherein the hydrophilic portion includes a first reactive member and a second reactive member, wherein the first reactive member of a first said amphiphilic compound interact with the second reactive member of a second said amphiphilic compound to covalently bond the hydrophilic portion of the first said amphiphilic compound to the hydrophilic portion of the second said amphiphilic compound. The invention further relates to a method of locking such a self assembled structure comprising:

providing a composition as above,
reacting a first reactive member of at least one of the plurality of amphiphilic compounds with a second reactive member of another of the plurality of amphiphilic compounds.

In embodiments, the self assembled structure of the invention is a linear micelle. In embodiments, the covalent bonds are radial. In embodiments, the covalent bonds extend longitudinally along the linear micelle. In embodiments, the self assembled structure comprises terminal reactive members available on the outer surface of the self assembled structure.

Accordingly, amphiphilic compounds are described herein which include a hydrophilic portion and a hydrophobic portion with the hydrophilic portion being functionalized with one or more first reactive members and one or more second reactive members, the second reactive members being complementary to the first reactive members. The complementary first and second reactive members of the amphiphilic compounds provide for the covalent attachment of adjacent amphiphilic compounds in a self-assembled structure when a first reactive member of one amphiphilic compound reacts with to a second reactive member of another amphiphilic compound. In embodiments, the hydrophilic portion of the amphiphilic compound includes a terminal reactive member in addition to the first and second reactive members.

Compositions in accordance with this disclosure include a plurality of such amphiphilic compounds in a solvent in a manner which provides for self assembling of the amphiphilic compounds. Once assembled, more than one amphiphilic compound having a hydrophilic portion functionalized with first reactive members and second reactive members are positioned near another so that first reactive members on one amphiphilic compound are able to react with second complementary reactive members on a neighboring amphiphilic compound to crosslink and chemically lock the composition in the self assembled shape. In embodiments, the self-assembled shape is a substantially spherical micelle. In other embodiments, the self-assembled shape is a substantially linear micelle or a nanofiber.

Methods for forming the compounds, compositions and self assembled shapes are also described.

An aspect of the invention is an amphiphilic compound comprising
a hydrophilic portion and a hydrophobic portion, the hydrophilic portion including a first reactive member and a second reactive, wherein the second reactive member is complementary to the first reactive member.

Another aspect of the invention is an amphiphilic compound comprising
a hydrophilic portion and a hydrophobic portion, the hydrophobic portion including a first reactive member and a second reactive, wherein the second reactive member is complementary to the first reactive member.

Another aspect of the invention is a composition comprising
a hydrophilic solvent;
optionally a catalyst;
a first amphiphilic compound having a hydrophilic portion and a hydrophobic portion, the hydrophilic portion including a plurality of first reactive members; and
a second amphiphilic compound having a hydrophilic portion and a hydrophobic portion, the hydrophilic portion including a plurality of a second reactive members, wherein the second reactive members are complementary to the first reactive members.

Another aspect of the invention is a self assembled structure comprising
a first amphiphilic compound having a hydrophilic portion and a hydrophobic portion, the hydrophilic portion including a plurality of first reactive members; and
a second amphiphilic compound having a hydrophilic portion and a hydrophobic portion, the hydrophilic portion including a plurality of a second reactive members, wherein the second reactive members are complementary to the first reactive members.

Another aspect of the invention is a self assembled structure comprising
a first amphiphilic compound having a hydrophilic portion and a hydrophobic portion;
a second amphiphilic compound having a hydrophilic portion and a hydrophobic portion, the hydrophilic portions of the first and second amphiphilic compound being adjacent to and covalently bound to each other.

The self assembled structure may be a linear micelle. The covalent bonds may be radial. The covalent bonds may extend longitudinally along the linear micelle.

Another aspect of the invention is a method of locking a self assembled structure comprising
combining a solvent and a plurality of amphiphilic compounds each having a hydrophilic portion and a hydrophobic portion, the hydrophilic portion of each amphiphilic compound including a first reactive member and a second reactive, wherein the second reactive members are complementary to the first reactive members, and
reacting a first reactive member of at least one of the plurality of amphiphilic compounds with a second reactive member of another of the plurality of amphiphilic compounds.

The amphiphilic compound may further comprise a terminal reactive member on the hydrophilic portion.

The self assembled structure may further comprise terminal reactive members available on the outer surface of the self assembled structure.

BRIEF DESCRIPTION OF THE DRAWINGS

FIGS. 1A and 1B schematically illustrates a functionalized amphiphilic compound in accordance with the present disclosure from a side view and top view, respectively; and FIG. 2 schematically illustrates a linear micelle or nanofiber in accordance with the present disclosure;

DETAILED DESCRIPTION OF PREFERRED EMBODIMENTS

Figure 3:
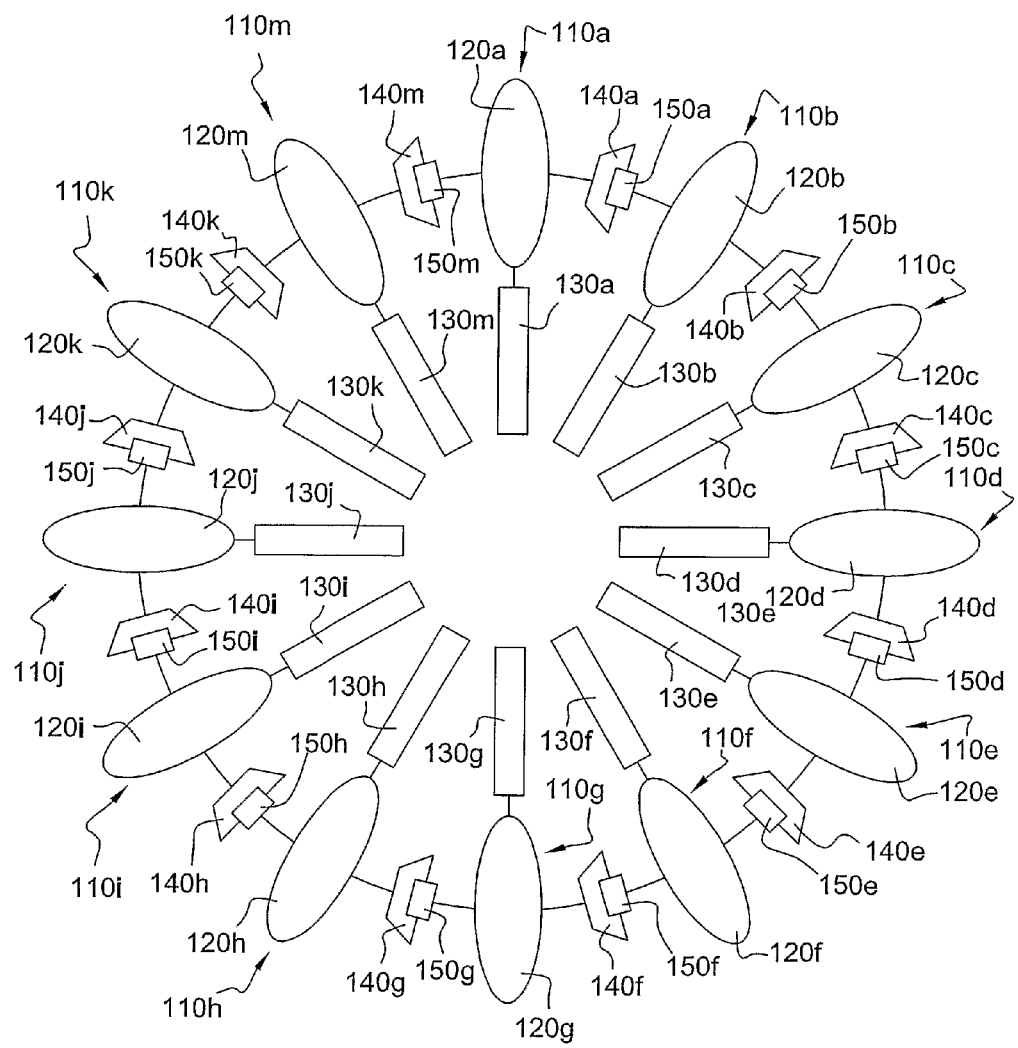
FIG. 3 schematically illustrates a cross section perpendicular to the axis of the linear micelle or nanofiber shown in FIG. 2.

As shown in FIGS. 1A and 1B, amphiphilic compound 10 in accordance with the present disclosure, includes hydrophilic portion 20 and hydrophobic portion 30 wherein hydrophilic portion 20 is functionalized with at least one (in this illustrative embodiment, two) first reactive members 40 and at least one (in this illustrative embodiment, two) second reactive members 50. Hydrophilic portion 20 and hydrophobic portion 30 are covalently bonded to one another directly or via a linker molecule 45. First reactive member 40 of one amphiphilic compound 10 is intended to react with complementary second reactive member 50 of another amphiphilic compound (not shown in FIG. 1) when positioned in proximity to one another. Optionally, hydrophilic portion 20 is functionalized with a terminal reactive member 60.

A plurality of amphiphilic compounds may be combined with a solvent to form a self-assembling composition. The compositions described herein include a solvent and a plurality of amphiphilic compounds, each compound including a hydrophilic portion and a hydrophobic portion. When added to a hydrophilic solvent, the amphiphilic compounds self-assemble to form a micelle, with the hydrophilic portions aligned along the exterior of the micelle and the hydrophobic portions gathered near the interior of the micelle. Under certain conditions, the micelle formed is a linear micelle or nanofiber. The first and second reactive members will react to provide stability to the self assembled structure. Where the self assembled structure is a linear micelle or nanofiber, first and second reactive members provide radial cross-linking as well as longitudinal cross-linking along the length of the linear micelle or nanofiber.

Turning now to FIG. 2, self assembled linear micelle or nanofiber 100 is schematically shown including an outer hydrophilic layer 102 defined by a collection hydrophilic portions of the amphiphilic compounds and an inner hydrophobic layer 104 defined by a collection hydrophilic portions of the amphiphilic compounds. For convenience, "A" refers to the longitudinal axis of linear micelle or nanofiber 10.

As seen in FIG. 3, in a cross-section perpendicular to axis A, linear micelle or nanofiber 10 is made up from a plurality of amphiphilic compounds 110a-110m, each of the compounds include hydrophilic portion 120a-120m and hydrophobic portion 130a-130m with each hydrophilic portion 120a-m functionalized with first reactive members 140a-m and second reactive members 150a-m. First reactive member 140a of amphiphilic compound 110a is shown crosslinked to second reactive member 150b of an adjacent amphiphilic compound 110b. Second reactive member 150a of amphiphilic compound 110a is also shown crosslinked to first reactive member 140m of still another amphiphilic compound 110m. The ability of the hydrophilic portions of a plurality of amphiphilic compounds to radially crosslink with other hydrophilic portions of amphiphilic compounds allows the self assembled structures described herein to be chemically locked into position, adding stability and strength to the self assembled structures described herein. The compositions described herein may include any number of chemical linkages to lock the composition into a self-assembled shape.

Figure 4:
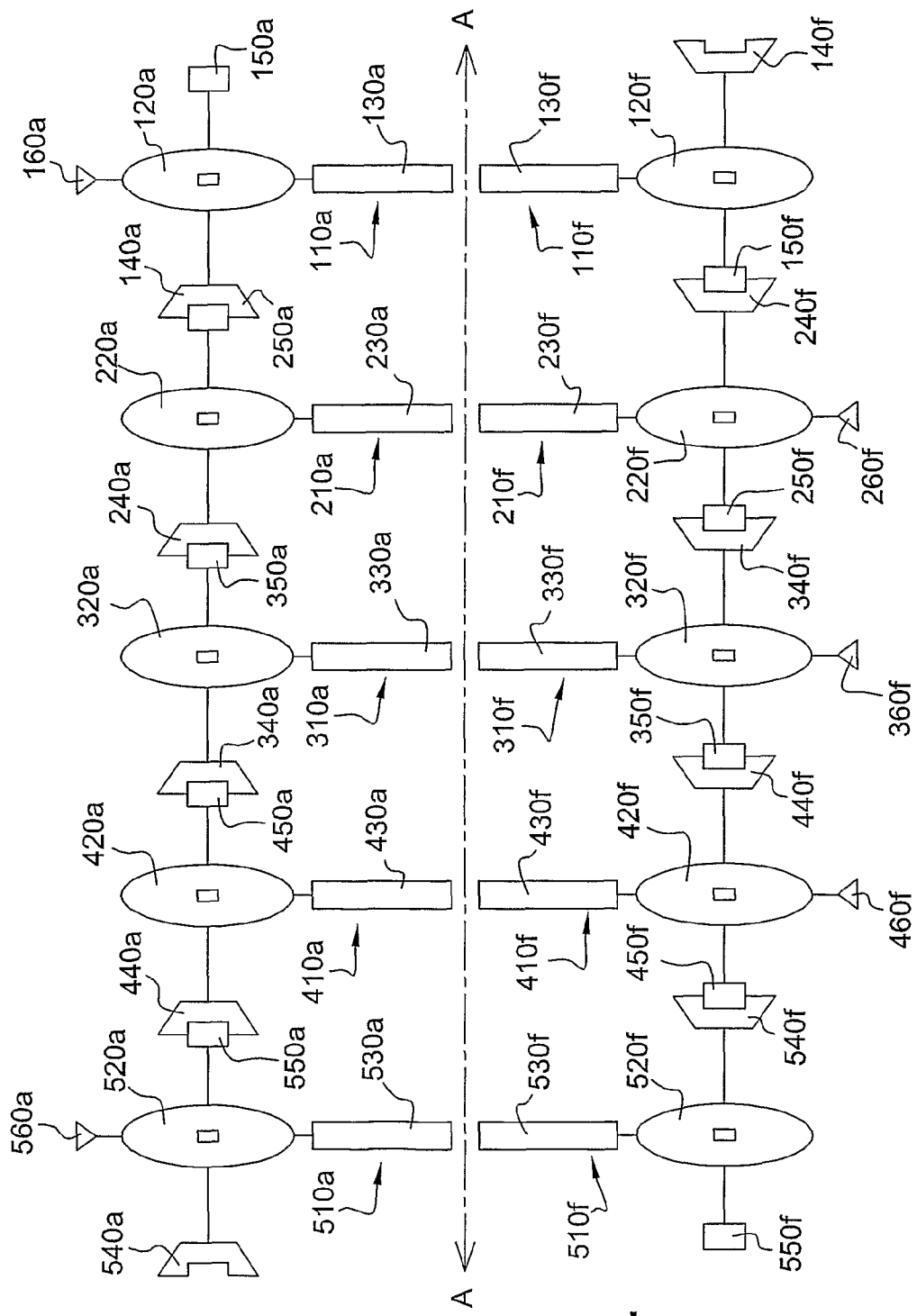
FIG. 4 schematically illustrates a cross section parallel to the axis of the linear micelle or nanofiber shown in FIG. 2.

As shown in FIG. 4, in a cross-section parallel to axis A adjacent amphiphilic compounds may also create linkages to provide longitudinal cross-linking along the length of the linear micelle or nanofiber. For example, amphiphilic compounds 110a and 110f covalently bond via reactive members 140a and 150f to adjacent amphiphilic compounds 210a and 210f via reactive members 250a and 240f. Likewise, amphiphilic compounds 210a and 210f covalently bond via reactive members 240a and 250f to adjacent amphiphilic compounds 310a and 310f via reactive members 350a and 340f, and so on along the length of the self assembled linear micelle or nanofiber. Optional terminal reactive members 160a, 260f, 360f, 460f and 560a provide reactive sites at the surface of the linear micelle or nanofiber. It should be understood, of course that optional terminal reactive members may, if desired, be provided on each hydrophilic portion of each amphiphilic compound.

The Amphiphilic Compound

The amphiphilic compound includes at least one portion which is hydrophilic and at least one portion which is hydrophobic. The terms "hydrophilic" and "hydrophobic" are generally defined in teal's of a partition coefficient P, which is the ratio of the equilibrium concentration of a compound in an organic phase to that in an aqueous phase. A hydrophilic compound has a log P value less than 1.0, typically less than about −0.5, where P is the partition coefficient of the compound between octanol and water, while hydrophobic compounds will generally have a log P greater than about 3.0, typically greater than about 5.0.

The amphiphilic compound may be linear, branched, block or graft copolymers. The hydrophilic portions are derived from hydrophilic polymers or compounds selected from the group consisting of polyamides, polyethylene oxide (PEO), polyurethanes, polylactones, polyethylene glycol, polyimides, polylactams, poly-vinyl-pyrrolidone, polyvinyl alcohols, polyacrylic acid, polymethacrylic acid, poly(hydroxyethyl methacrylate), gelatin, dextan, oligosaccharides, such as chitosan, hyaluronic acid, alginate, chondroitin sulfate, mixtures and combinations thereof. The hydrophobic portions are derived from hydrophobic polymers or compounds selected from the group consisting of polyethylene, polypropylene, polyurethanes, polyacrylates, polymethacrylates, fluoropolymers, polycaprolactone, polylactide, polyglycolide, phospholipids, and hydrophobic oligosaccharides, polyureas, poly(ethylene/-vinyl acetate), polyvinylchloride, polyesters, polyamides, polycarbonate, polystyrenes, polytetrafluoroethylene, silicones, siloxanes, fatty acids, and chitosan having high degrees of acetylation over about 30%, in embodiments about 40 to about 60%, and mixtures and combinations thereof. The amphiphilic compound may include any biocompatible combination of hydrophilic and hydrophobic portions.

In embodiments, the amphiphilic compound may include a hydrophobic portion derived from a fatty acid, some non-limiting examples include saturated fatty acids, monoenoic fatty acids, polyenoic fatty acids, methylene-interrupted polymethylene-interrupted, conjugated, allenic acids, cumulenic acids, acetylenic fatty acids, hydroxy fatty acids, dicarboxylic acids, fatty acid carbonates, divinyl ether fatty acids, sulfur containing fatty acids, fatty acid amides, methoxy and acetoxy fatty acids, keto fatty acids, aldehydic fatty acids, halogenated fatty acids (F, Cl, Br), nitrated fatty acids, arsenic containing fatty acids, branched-chain fatty acids, mono or multibranched chain fatty acids, branched methoxy fatty acids, branched hydroxy fatty acids, ring containing fatty acids, cyclopropane acids, cyclobutane acids, cyclopentenyl acids, furanoid acids, cyclohexyl acids, phenylalkanoic acids, epoxy acids, cyclic fatty peroxides, lipoic acids and combinations thereof. Examples of saturated fatty acids include butanoic, pentanoic, hexanoic, octanoic, nonanoic, decanoic, dodecanoic, tetradecanoic, hexadecanoic, heptadecanoic, octadecanoic, eicosanoic, docosanoic, tetracosanoic, hexacosanoic, heptacosanoic, and octacosanoic. In embodiments, the fatty acid may include one of the following formulas: $C_6H_{11}O$, $C_{10}H_{19}O$, $C_{16}H_{31}O$, $C_{22}H_{43}O$. The amphiphilic compound may also includes a hydrophilic portion derived from an oligosaccharide such as chitosan, hyaluronic acid, alginates or chondroitin sulfate.

Chitosan is a natural polysaccharide comprising copolymers of glucosamine and N-acetylglucosamine, and can be obtained by the partial acetylation of chitin, from any source (e.g., crustacean shells, squid pen, and mushrooms), the second most abundant natural polymer after cellulose. The process of acetylation involves the removal of acetyl groups from the molecular chain of chitin, leaving behind a complete amino group ($-NH_2$) and chitosan versatility depends mainly on this high degree chemical reactive amino groups. As the degree of acetylation increases, the more hydrophobic the chitosan becomes. Conversely, as the degree of acetylation decreases, the more hydrophilic the chitosan becomes under a pH<6. Thus, in some embodiments, chitosan oligomers displaying different degrees of acetylation may be combined to form an amphiphilic compound. Moreover, in some embodiments in which more than one oligosaccharide may be utilized to form the amphiphilic compound, the degree of acetylation of the chitosan oligomers may be altered depending on the hydrophilicity of the other oligosaccharides. For instance, the amphiphilic compound may include a hydrophilic portion derived from a chitosan oligomer having a low degree of acetylation, ranging from about 0 to about 30%, and a hydrophobic portion derived from a chitosan oligomer having a higher degree of acetylation, greater than about 50% at a pH<6. Alternatively, the amphiphilic compound may be formed under a raised pH (pH>7) such that the compound includes a hydrophobic portion derived from a chitosan oligomer having a low degree of acetylation, ranging from about 0 to about 10%, and a hydrophilic portion derived from a hyaluronic acid oligomer or alginate oligomer which under the raised pH conditions displays a negative charge. Under the raised pH conditions, the chitosan oligomer having a low degree of acetylation displays a positive charge and becomes more hydrophilic.

In still other embodiments, a fatty acid hydrophobic portion may be combined with a hydrophilic peptide or drug. Some non-limiting examples of hydrophilic polypeptides or drugs include oxytocin, vasopressin, adrenocorticotrophic hormone (ACTH), epidermal growth factor (EGF), transforming growth factor antagonists, prolactin, luliberin or luteinizing hormone releasing hormone (LH-RH), LH-RH agonists or antagonists, growth hormone, growth hormone releasing factor, insulin, somatostatin, bombesin antagonists, glucagon, interferon, gastrin, tetragastrin, pentagastrin, urogastrone, secretin, calcitonin, enkephalins, endorphins, angiotensins, renin, bradykinin, bacitracins, polymyzins, colistins, tyrocidin, gramicidines, and synthetic analogues and modifications and pharmaceutically-active fragments thereof, monoclonal antibodies and soluble vaccines.

In still other embodiments, the amphiphilic compound includes a hydrophobic oligosaccharide bonded to a hydrophilic oligosaccharide. Some non-limiting examples of hydrophilic oligosaccharides include chitosan, hyaluronic acid, alginates and chondroitin.

The Solvent

The solvents to be combined with the amphiphilic compounds to form the self-assembled structures may be any suitable solvent which thermodynamically is a good solvent for one portion of the compound and a poor solvent for the other portion of the compound. Where it is desired for the self assembled structure to have the hydrophilic portion on the outside thereof, the solvent chosen should be aqueous or at least hydrophilic. In such embodiments, the hydrophilic portion of the amphiphilic compound is functionalized with reactive groups as described herein. It should be understood however, that it is also possible to functionalize the hydrophobic portion of the amphiphilic compound and combine such compounds with a hydrophobic solvent when it is desired that the self assembled structure to have the hydrophobic portion on the outside thereof.

Thus, in embodiments, the solvent employed in making the present compositions are hydrophilic. It is contemplated that combinations of solvents may be employed. Suitable hydrophilic solvents of the present disclosure are selected from, but are not limited to lower alcohols such as ethanol, and polyhydric alcohols such as propylene glycol, butylene glycol, hexylene glycol, glycerin, sorbitol; polyethylene glycols of MW (molecular weight) less than 30,000, in embodiments less than 10,000; and polypropylene glycols of MW less than 5,000, in embodiments less than 1,000. Specific illustrative examples include, but are not limited to, diethylene glycol monoethyl ether, ethanol, glycerin, glycofurol, a MPEG, N-methyl-2-pyrrolidone, a PEG, propylene carbonate, propylene glycol, or a mixture of any two or more thereof. In some embodiments, the PEG has an average molecular weight of from about 100 g/mol to about 1,000 g/mol. In some embodiments, the MPEG has an average molecular weight of from about 100 g/mol to about 1,000 g/mol. In some embodiments, the hydrophilic solvent is ethanol, a PEG, or a mixture of any two or more thereof. In some such embodiments, the ethanol is present at a concentration of up to about 15% based upon the total weight of the formulation. In other such embodiments, the PEG is present at a concentration of up to about 90% based upon the total weight of the formulation.

In embodiments where a hydrophobic solvent is used, hydrophobic solvents which may be used are virtually all water-immiscible liquids which do not interfere with the self assembly of the amphiphilic compound. Solvents suitable include aliphatic and aromatic hydrocarbons or their mixtures. Suitable aliphatic hydrocarbons are, for example, pentane, hexane, heptane, octane, nonane, decane, cyclohexane, decalin, methylcyclohexane, isooctane and ethylcyclohexane. Suitable aromatic hydrocarbons are, for example, benzene, toluene, xylene and isopropylbenzene. In addition, it is also possible to use halogenated hydrocarbons, such as tetrachloroethane, hexachloroethane, trichloroethane and chlorobenzene. In addition, aliphatic esters, such as ethyl acetate, are suitable. Lipophilic solvents suitable for use in such embodiments may include, but are not limited to a fatty acid such as, but no limited to, linoleic, linolenic, oleic, palmitostearic acid, and stearic acid; a medium chain glyceride such as, but not limited to, glyceryl mono-, di-, or tri-caprylic and capric acid esters, also known as medium chain mono-, di-, and triglycerides; long chain glyceride (of C12-C18 fatty acids) such as, but not limited to, corn oil; cottonseed oil, glyceryl behenate, glyceryl monooleate, glyceryl monostearate, glyceryl palmitostearate, olive oil, peanut oil, peppermint oil, safflower oil, sesame oil, and soybean oil; a ethyl ester of a fatty acid such as ethyl linoleate and ethyl oleate; α-tocopherol; a propylene glycol fatty acid ester such as, but not limited to, propylene glycol mono- or di-laureate; a sorbitan fatty acid ester such as, but not limited to, sorbitan monolaurate, sorbitan monooleate, sorbitan monopalmitate, sorbitan monostearate, and sorbitan trioleate; a polyglyceryl fatty acid ester formed from various glyceryl ethers and fatty acids. In some embodiments, the lipophilic solvent is oleic acid. Examples of polyglycerols used in esterification include diglycerol, tetraglycerol, hexaglycerol, decaglycerol, decaglycerol, and the like. Examples of fatty acids reacted with polyglycerols include oleic acid, linoleic acid, stearic acid, and the like. Examples of polyglyceryl fatty acid ester include polyglyceryl oleate; polyglyceryl palmitostearate; diglyceryl monooleate; tetraglyceryl monooleate; hexaglyceryl monooleate; hexaglyceryl pentaoleate; decaglyceryl pentaoleate; decaglyceryl decaoleate and the like.

The First and Second Reactive members

In order to covalently bond the hydrophilic portions of an amphiphilic compound to other hydrophilic portions of additional amphiphilic compounds, the hydrophilic portions of the amphiphilic compounds are functionalized with one or more first reactive members and one or more second reactive members. The first and second reactive members are complementary. By "complementary" it is meant that the first and second reactive members are able to interact with one another to covalently bond the hydrophilic portion of one amphiphilic compound to the hydrophilic portion of another amphiphilic compound.

In embodiments, the hydrophilic portions of a plurality of amphiphilic compounds are functionalized with both electrophilic and nucleophilic functional groups, such that, for example, a nucleophilic functional group on the hydrophilic portion of an amphiphilic compound may react with an electrophilic functional group on the hydrophilic portion of a different amphiphilic compound to form a covalent bond between the two amphiphilic compounds.

Virtually any nucleophilic group can be used to functionalize the amphiphilic compounds, so long as a reaction can occur with the electrophilic group on the hydrophilic portion of another amphiphilic compound. Analogously, virtually any electrophilic group can be used to functionalize the hydrophilic portion of the amphiphilic compound, so long as reaction can take place with the nucleophilic group on the hydrophilic portion of another amphiphilic compound. In embodiments, the reaction occurs without need for ultraviolet or other radiation. In embodiments, the reactions between the complementary groups should be complete in under 60 minutes, in embodiments under 30 minutes, in yet other embodiments, the reaction occurs in about 5 to 15 minutes or less.

Non-limiting examples of nucleophilic groups include, but are not limited to, $-NH_2$, $-NHR$, $-N(R)_2$, $-SH$, $-OH$, $-COOH$, $-C_6H_4-OH$, $-PH_2$, $-PHR$, $-P(R)_2$, $-NH-NH_2$, $-CO-NH-NH_2$, $-C_5H_4N$, etc. wherein R is hydrocarbyl, typically $C_1$-$C_4$ alkyl or monocyclic aryl. Organometallic moieties are also useful nucleophilic groups for the purposes of this disclosure, particularly those that act as carbanion donors. Examples of organometallic moieties include: Grignard functionalities —RMgHal wherein R is a carbon atom (substituted or unsubstituted), and Hal is halo, typically bromo, iodo or chloro; and lithium-containing functionalities, typically alkyllithium groups; sodium-containing functionalities.

It will be appreciated by those of ordinary skill in the art that certain nucleophilic groups must be activated with a base so as to be capable of reaction with an electrophile. For example, when there are nucleophilic sulfhydryl and hydroxyl groups on the amphiphilic compounds, the composition must be admixed with an aqueous base in order to remove a proton and provide an $-S^-$ or $-O^-$ species to enable reaction with an electrophile. Unless it is desirable for the base to participate in the reaction, a non-nucleophilic base is used. In some embodiments, the base may be present as a component of a buffer solution.

The selection of electrophilic groups provided on the hydrophilic portion of the amphiphilic compound is made so that reaction is possible with the specific nucleophilic groups on the hydrophilic portion of another amphiphilic compound. Thus, when the hydrophilic portion of an amphiphilic compound is functionalized with amino groups, the hydrophilic portion of another amphiphilic compound is functionalized with groups selected so as to react with amino groups. Analogously, when the surface of the hydrophilic portion of an amphiphilic compound is functionalized with sulfhydryl moieties, the corresponding electrophilic groups are sulfhydryl-reactive groups, and the like.

By way of example, when the hydrophilic portion of an amphiphilic compound is functionalized with amino groups (generally although not necessarily primary amino groups), the electrophilic groups present on the hydrophilic portion of another amphiphilic compound are amino reactive groups such as, but not limited to: (1) carboxylic acid esters, including cyclic esters and "activated" esters; (2) acid chloride groups ($-CO-Cl$); (3) anhydrides ($-(CO)-O-(CO)-R$); (4) ketones and aldehydes, including $\alpha\beta$-unsaturated aldehydes and ketones such as $-CH=CH-CH=O$ and $-CH=CH-C(CH_3)=O$; (5) halides; (6) isocyanate ($-N=C=O$); (7) isothiocyanate ($-N=C=S$); (8) epoxides; (9) activated hydroxyl groups (e.g., activated with conventional activating agents such as carbonyldiimidazole or sulfonyl chloride); and (10) olefins, including conjugated olefins, such as ethenesulfonyl ($-SO_2CH=CH_2$) and analogous functional groups, including acrylate ($-CO_2-C=CH_2$), methacrylate ($-CO_2-C(CH_3)=CH_2$)), ethyl acrylate ($-CO_2-C(CH_2CH_3)=CH_2$), and ethyleneimino ($-CH=CH-C=NH$). Since a carboxylic acid group per se is not susceptible to reaction with a nucleophilic amine, components containing carboxylic acid groups must be activated so as to be amine-reactive. Activation may be accomplished in a variety of ways, but often involves reaction with a suitable hydroxyl-containing compound in the presence of a dehydrating agent such as dicyclohexylcarbodiimide (DCC) or dicyclohexylurea (DHU). For example, a carboxylic acid can be reacted with an alkoxy-substituted N-hydroxy-succinimide or N-hydroxysulfosuccinimide in the presence of DCC to form reactive electrophilic groups, the N-hydroxysuccinimide ester and the N-hydroxysulfosuccinimide ester, respectively. Carboxylic acids may also be activated by reaction with an acyl halide such as an acyl chloride (e.g., acetyl chloride), to provide a reactive anhydride group. In a further example, a carboxylic acid may be converted to an acid chloride group using, e.g., thionyl chloride or an acyl chloride capable of an exchange reaction. Specific reagents and procedures used to carry out such activation reactions will be known to those of ordinary skill in the art and are described in the pertinent texts and literature.

Analogously, when the hydrophilic portion of an amphiphilic compound is functionalized with sulfhydryl, the electrophilic groups present on the hydrophilic portion of another amphiphilic compound are groups that react with a sulfhydryl moiety. Such reactive groups include those that form thioester linkages upon reaction with a sulfhydryl group, such as those described in PCT Publication No. WO 00/62827 to Wallace et al. As explained in detail therein, such "sulfhydryl reactive" groups include, but are not limited to: mixed anhydrides; ester derivatives of phosphorus; ester derivatives of p-nitrophenol, p-nitrothiophenol and pentafluorophenol; esters of substituted hydroxylamines, including N-hydroxyphthalimide esters, N-hydroxysuccinimide esters, N-hydroxysulfosuccinimide esters, and N-hydroxyglutarinide esters; esters of 1-hydroxybenzotriazole; 3-hydroxy-3,4-dihydro-benzotriazin-4-one; 3-hydroxy-3,4-dihydro-quinazoline-4-one; carbonylimidazole derivatives; acid chlorides; ketenes; and isocyanates. With these sulfhydryl reactive groups, auxiliary reagents can also be used to facilitate bond formation, e.g., 1-ethyl-3-[3-dimethylaminopropyl]carbodiimide can be used to facilitate coupling of sulfhydryl groups to carboxyl-containing groups.

In addition to the sulfhydryl reactive groups that form thioester linkages, various other sulfydryl reactive functionalities can be utilized that form other types of linkages. For example, compounds that contain methyl imidate derivatives form imido-thioester linkages with sulfhydryl groups. Alternatively, sulthydryl reactive groups can be employed that form disulfide bonds with sulfhydryl groups, such groups generally have the structure $-S-S-Ar$ where Ar is a substituted or unsubstituted nitrogen-containing heteroaromatic moiety or a non-heterocyclic aromatic group substituted with an electron-withdrawing moiety, such that Ar may be, for example, 4-pyridinyl, o-nitrophenyl, m-nitrophenyl, p-nitrophenyl, 2,4-dinitrophenyl, 2-nitro-4-benzoic acid, 2-nitro-4-pyridinyl, etc. In such instances, auxiliary reagents, i.e., mild oxidizing agents such as hydrogen peroxide, can be used to facilitate disulfide bond formation.

Yet another class of sulfhydryl reactive groups forms thio-ether bonds with sulthydryl groups. Such groups include, inter alia, maleimido, substituted maleimido, haloalkyl, epoxy, imino, and aziridino, as well as olefins (including conjugated olefins) such as ethenesulfonyl, etheneimino, acrylate, methacrylate, and ($\alpha,\beta$-unsaturated aldehydes and ketones.

It will also be appreciated that certain functional groups can react as nucleophiles or as electrophiles, depending on the selected reaction partner and/or the reaction conditions. For example, a carboxylic acid group can act as a nucleophile in the presence of a fairly strong base, but generally acts as an electrophile allowing nucleophilic attack at the carbonyl carbon and concomitant replacement of the hydroxyl group with the incoming nucleophile.

Table 1, below illustrates, solely by way of example, representative complementary pairs of electrophilic and nucleophilic functional groups that may be employed in functionalizing the hydrophilic portion of amphiphilic compounds with first reactive members (in Table 1 both $R_1$ and $R_2$ represent the hydrophilic portion of amphiphilic compounds).

TABLE 1

| REPRESENTATIVE NUCLEOPHILIC COMPONENT (A, $FN_{NU}$) | REPRESENTATIVE ELECTROPHILIC COMPONENT (B, $FN_{EL}$) | RESULTING LINKAGE |
|---|---|---|
| $R^1$—$NH_2$ | $R^2$—O—(CO)—O—N(COCH$_2$) (succinimidyl carbonate terminus) | $R^1$—NH—(CO)—O—$R^2$ |
| $R^1$—SH | $R^2$—O—(CO)—O—N(COCH$_2$) | $R^1$—S—(CO)—O—$R^2$ |
| $R^1$—OH | $R^2$—O—(CO)—O—N(COCH$_2$) | $R^1$—S—(CO)—$R^2$ |
| $R^1$—$NH_2$ | $R^2$—O(CO)—CH=CH$_2$ (acrylate terminus) | $R^1$—NH—CH$_2$CH$_2$—(CO)—O—$R^2$ |
| $R^1$—SH | $R^2$—O—(CO)—CH=CH$_2$ | $R^1$—S—CH$_2$CH$_2$—(CO)—O—$R^2$ |
| $R^1$—OH | $R^2$—O—(CO)—CH=CH$_2$ | $R^1$—O—CH$_2$CH$_2$—(CO)—O—$R^2$ |
| $R^1$—$NH_2$ | $R^2$—O(CO)—(CH$_2$)$_3$—CO$_2$N(COCH$_2$) (succinimidyl glutarate terminus) | $R^1$—NH—(CO)—(CH$_2$)$_3$—(CO)—O$R^2$ |
| $R^1$—SH | $R^2$—O(CO)—(CH$_2$)$_3$—CO$_2$—N(COCH$_2$) | $R^1$—S—(CO)—(CH$_2$)$_3$—(CO)—O$R^2$ |
| $R^1$—OH | $R^2$—O(CO)—(CH$_2$)$_3$—CO$_2$—N(COCH$_2$) | $R^1$—O—(CO)—(CH$_2$)$_3$—(CO)—O$R^2$ |
| $R^1$—$NH_2$ | $R^2$—O—CH$_2$—CO$_2$—N(COCH$_2$) (succinimidyl acetate terminus) | $R^1$—NH—(CO)—CH$_2$—O$R^2$ |
| $R^1$—SH | $R^2$—O—CH$_2$—CO$_2$—N(COCH$_2$) | $R^1$—S—(CO)—CH$_2$—O$R^2$ |
| $R^1$—OH | $R^2$—O—CH$_2$—CO$_2$—N(COCH$_2$) | $R^1$—O—(CO)—CH$_2$—O$R^2$ |
| $R^1$—$NH_2$ | $R^2$—O—NH(CO)—(CH$_2$)$_2$—CO$_2$—N(COCH$_2$) (succinimidyl succinamide terminus) | $R^1$—NH—(CO)—(CH$_2$)$_2$—(CO)—NH—O$R^2$ |
| $R^1$—SH | $R^2$—O—NH(CO)—(CH$_2$)$_2$—CO$_2$—N(COCH$_2$) | $R^1$—S—(CO)—(CH$_2$)$_2$—(CO)—NH—O$R^2$ |
| $R^1$—OH | $R^2$—O—NH(CO)—(CH$_2$)$_2$—CO$_2$—N(COCH$_2$) | $R^1$—O—(CO)—(CH$_2$)$_2$—(CO)—NH—O$R^2$ |
| $R^1$—$NH_2$ | $R^2$—O—(CH$_2$)$_2$—CHO (propionaldehyde terminus) | $R^1$—NH—(CO)—(CH$_2$)$_2$—O$R^2$ |
| $R^1$—$NH_2$ | 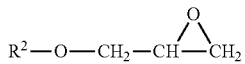 (glycidyl ether terminus) | $R^1$—NH—CH$_2$—CH(OH)—CH$_2$—O$R^2$ and $R^1$—N[CH$_2$—CH(OH)—CH$_2$—O$R^2$]$_2$ |
| $R^1$—$NH_2$ | $R^2$—O—(CH$_2$)$_2$—N=C=O (isocyanate terminus) | $R^1$—NH—(CO)—NH—CH$_2$—O$R^2$ |
| $R^1$—$NH_2$ | $R^2$—SO$_2$—CH=CH$_2$ (vinyl sulfone terminus) | $R^1$—NH—CH$_2$CH$_2$—SO$_2$—$R^2$ |
| $R^1$—SH | $R^2$—SO$_2$—CH=CH$_2$ | $R^1$—S—CH$_2$CH$_2$—SO$_2$—$R^2$ |

When the hydrophilic portion of an amphiphilic compound is functionalized with —OH, the electrophilic functional groups on the hydrophilic portion of another amphiphilic compound must react with hydroxyl groups. The hydroxyl group may be activated as described above with respect to carboxylic acid groups, or it may react directly in the presence of base with a sufficiently reactive electrophile such as an epoxide group, an aziridine group, an acyl halide, or an anhydride.

When the hydrophilic portion of an amphiphilic compound is functionalized with an organometallic nucleophile such as a Grignard functionality or an alkyllithium group, suitable electrophilic functional groups for reaction therewith are those containing carbonyl groups, including, by way of example, ketones and aldehydes.

In embodiments, the hydrophilic portion of an amphiphilic compound is functionalized with first click-reactive members and second click-reactive members complementary to the first click-reactive members. The "click-reactive members" are meant to include those reactive members used in the processes known to those skilled in the art as Click chemistry.

Click chemistry refers to a collection of reactive members having a high chemical potential energy capable of producing highly selective, high yield reactions. The reactive members react to form extremely reliable molecular connections in most solvents, including physiologic fluids, and often do not interfere with other reagents and reactions. Examples of click chemistry reactions include Huisgen cycloaddition, Diels-Alder reactions, thiol-alkene reactions, and maleimide-thiol reactions.

Huisgen cycloaddition is the reaction of a dipolarophile with a 1,3-dipolar compound that leads to 5-membered (hetero)cycles. Examples of dipolarophiles are alkenes and alkynes and molecules that possess related heteroatom functional groups (such as carbonyls and nitriles). 1,3-Dipolar compounds contain one or more heteroatoms and can be described as having at least one mesomeric structure that represents a charged dipole. They include nitril oxides, azides, and diazoalkanes. Metal catalyzed click chemistry is an extremely efficient variant of the Huisgen 1,3-dipolar cycloaddition reaction between alkyl-aryly-sulfonyl azides, C—N triple bonds and C—C triple bonds which is well-suited herein. The results of these reactions are 1,2 oxazoles, 1,2,3 triazoles or tetrazoles. For example, 1,2,3 triazoles are formed by a copper catalyzed Huisgen reaction between alkynes and alkly/aryl azides. Metal catalyzed Huisgen reactions proceed at ambient temperature, are not sensitive to solvents, i.e., nonpolar, polar, semipolar, and are highly tolerant of functional groups. Non-metal Huisgen reactions (also referred to as strain promoted cycloaddition) involving use of a substituted cyclooctyne, which possesses ring strain and electron-withdrawing substituents such as fluorine, that together promote a [3+2] dipolar cycloaddition with azides are especially well-suited for use herein due to low toxicity as compared to the metal catalyzed reactions. Examples include DIFO (difluorinated cyclooctyne) and DIMAC (6,7-dimethoxyazacyclooct-4-yne). Reaction of the alkynes and azides is very specific and essentially inert against the chemical environment of biological tissues. One reaction scheme may be represented as:

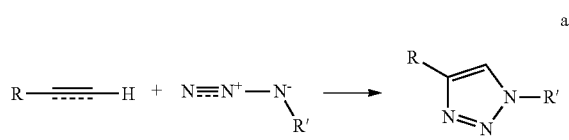

a)

where R and R' are amphiphilic compounds.

The Diels-Alder reaction combines a diene (a molecule with two alternating double bonds) and a dienophile (an alkene) to make rings and bicyclic compounds. Examples include:

Dienes

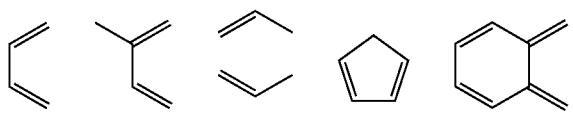

Dienophiles

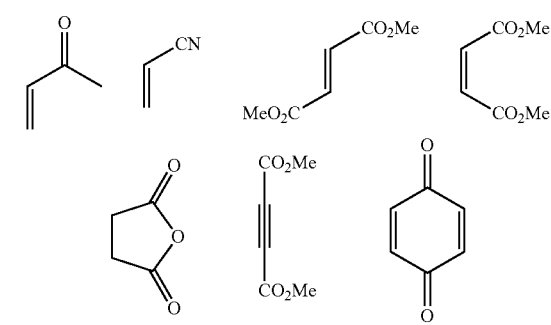

The thiol-alkene (thiol-ene) reaction is a hydrothiolation, i.e., addition of RS—H across a C=C bond. The thiol-ene reaction proceeds via a free-radical chain mechanism. Initiation occurs by radical formation upon UV excitation of a photoinitiator or the thiol itself. Thiol-ene systems form ground state charge transfer complexes and therefore photopolymerize even in the absence of initiators in reasonable polymerization times. However, the addition of UV light increases the speed at which the reaction proceeds. The wavelength of the light can be modulated as needed, depending upon the size and nature of the constituents attached to the thiol or alkene. A general thiol-ene coupling reaction mechanism is represented below:

Initiation

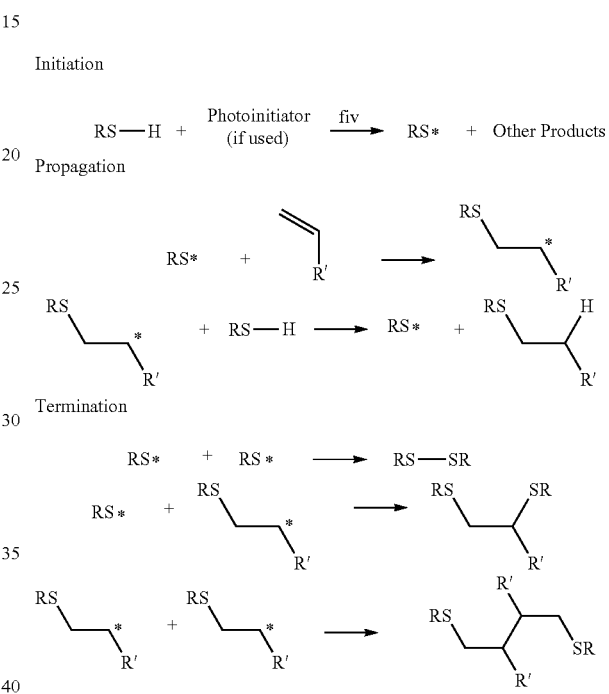

In embodiments, the hydrophilic portion of the amphiphilic compounds are functionalized to include first click-reactive members which include alkyne groups and second click-reactive members which include azide groups. In yet other embodiments, the hydrophilic portion of the amphiphilic compounds are functionalized to include first click-reactive members which include azide groups and a second click-reactive members which include alkene groups. See, van Berkel et al. *CemBioChem*, 8, pages 1504-1508 (2007).

The first and second click-reactive members are intended to react and covalently bond the hydrophilic portions of one amphiphilic compound to the hydrophilic portion of another, adjacent amphiphilic compound of the self assembled structure at a physiologic pH. However, in some embodiments, the first and second click-reactive members may react quicker or more completely following the addition of a catalyst, such as a pH modifier, a metal ion catalyst or the introduction of heat or radiation. In embodiments, the addition of UV radiation may enhance the formation of a covalent bond between the first and second click-reactive members. In embodiments, the addition of a metal catalyst, e.g., transition metal ions such as copper ions, may assist with the formation of a covalent bond between the first and second click-reactive members.

Functionalizing the Amphiphilic Compound

The first and second reactive members may be positioned on the hydrophilic portion of the amphiphilic compound using any variety of suitable chemical processes. It is contemplated that a plurality of first reactive members and second reactive members may be present located along the length of the hydrophilic portion of the amphiphilic compound.

In embodiments, the first and second reactive members are orthogonally positioned on the hydrophilic portions of the compounds. (See FIGS. 1A and 1B.) In the orthogonal position, the first and second reactive members are more likely to be in close proximity to one another when a plurality of the amphiphilic compounds are combined with a solvent to form the self-assembled composition.

In embodiments, the hydrophilic portion of the amphiphilic compound is functionalized after it has been combined with the hydrophobic portion of the compound. For example, the amphiphilic compounds can be functionalized after the hydrophilic portion is covalently bonded to the hydrophobic portion of the compound.

In embodiments where the hydrophilic portion is based on a hydrophilic peptide (e.g., peptides that bear a charge), azide groups may be provided by conversion of the amino acid methyl ester to the corresponding azide via a Cu(II)-catalyzed diazotransfer reaction using triflic azide as shown in the following reaction scheme:

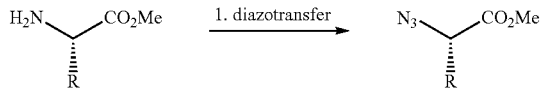

In embodiments where the hydrophilic portion is based on an oligosaccharide, the reactive members can be attached using the following reaction scheme as described in detail in Zhang et al., Helvetica Chimica Acta—Vol. 91 pages 608-617 (2008):

In embodiments where the hydrophobic portion of the amphiphilic compound is functionalized (e.g., those embodiments where a hydrophobic solvent is used to prepare the self assembled structures), the functionalized hydrophobic portion of the amphiphilic polymer may be formed from monomeric or polymeric materials prior to be combined with the hydrophilic portion of the compound. For example, the monomers from which the hydrophobic portion of the amphiphilic compound is made can be functionalized so that the reactive members appear along the length of the hydrophobic portion. In such embodiments, the monomers can be initially functionalized with a group such as a halogen to provide a reactive site at which the desired first reactive member can be attached after polymerization. Thus, for example, a cyclic lactone (e.g., glycolide, lactide, caprolactone, etc.) can be halogenated and then polymerized using known techniques for ring opening polymerization. Once polymerized, the halogenated sites along the resulting polyester chain can be functionalized with the first reactive member. For example, the halogenated polyester can be reacted with sodium azide to provide azide groups along the polymer chain or with propagyl alcohol to provide alkyne groups along the polymer chain. See, R. Riva et al., *Polymer* 49, pages 2023-2028 (2008) for a description of such reaction schemes. Alternatively, a pre-formed biodegradable polyester portion can be halogenated by reaction with a non-nucleophilic strong base, such as lithium diisopropylamide, followed by electrophilic substitution with iodine chloride. The halogenated polyester is then reacted with sodium azide or propagyl alcohol to provide azide or alkyne groups, respectively. In another example, a propargyl group may be introduce into a cyclic carbonate monomer to form 5-methyl-5-propargyloxycarbonyl-1,3-dioxan-2-one (MPC) which is polymerizable with lactide to form p(LA-co-MPC). See, Q. Shi et al., *Biomaterials,* 29, pages 1118-1126 (2008). Other methods for functionalizing lactones are described in Jérôme et al., *Advanced Drug Deliver Reviews,* 60, pages 1056-1076 (2008). The entire disclosure of each of these articles is incorporated herein by this reference.

As another example, where the hydrophobic portion is based on a fatty acid, azide groups can be attached using the following synthetic route:

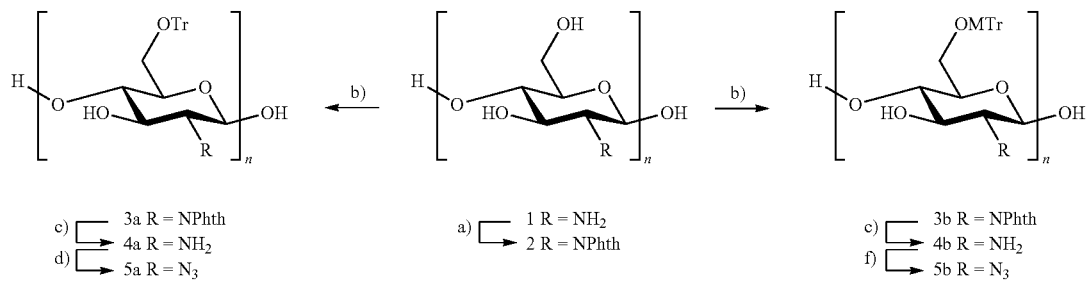

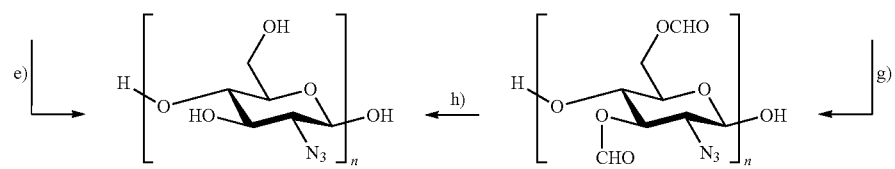

Scheme 1. Synthetic Route to Head Group Azide-Tagged Diacylglycerol Scaffold 2

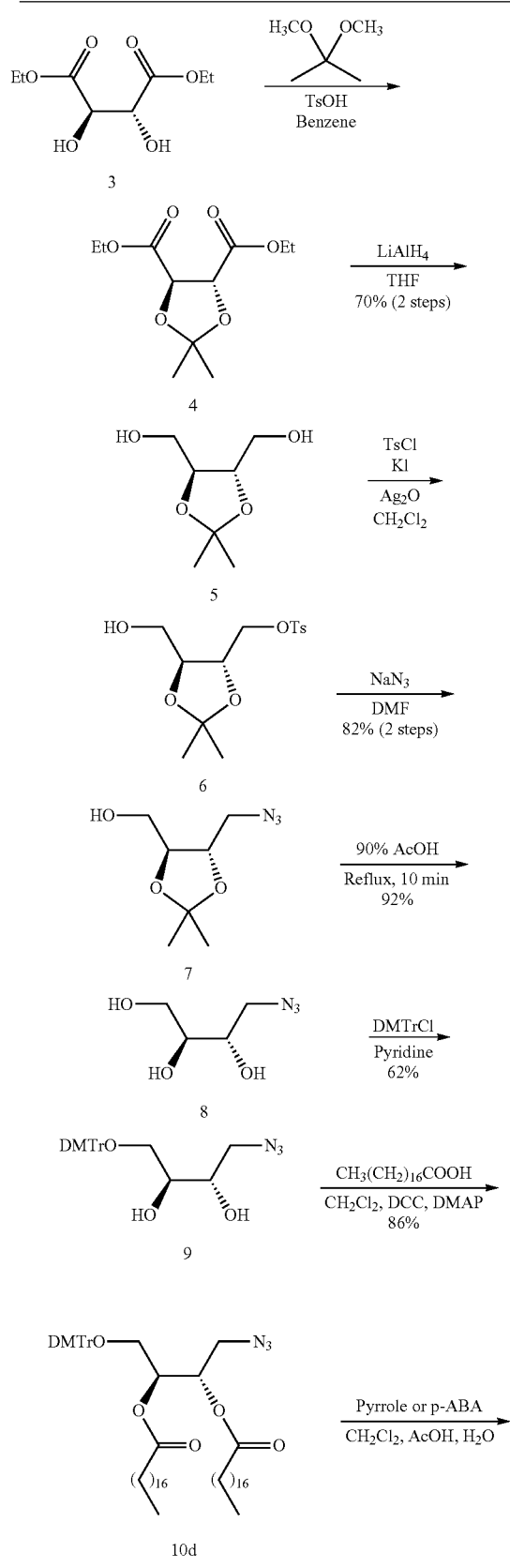

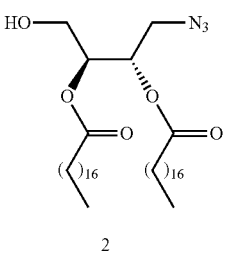

In embodiments, the acids used to introduce the acyl chains (10d) may be dicarboxylic acid fatty acids which provide for the synthesis of di-azide compounds.

In embodiments, a plurality of different first and second reactive members may be positioned on each of the hydrophilic portions of the amphiphilic compounds.

In embodiments, a terminal functionality, also called in the present application terminal reactive member, is provided on the hydrophilic portion of the amphiphilic compound. This terminal functionality should not be complementary to either the first or second reactive members. These terminal reactive members will be positioned on the outside surface of the self assembled structure and can provide a means for further reaction of the self assembled structure with other reactive entities bearing a reactive member that is complementary to the terminal reactive member, thus providing the self assembled structure with an activated surface.

The self assembled structures having an activated surface in accordance with the present disclosure can be used for a variety of purposes. For example, in embodiments they may be used for drug delivery. In such embodiments, the drug to be delivered is functionalized with one or more reactive members that are complementary to the terminal reactive members provided on the surface of the self assembled structure. In this manner, the reactive members on the drug to be delivered are able to interact with the terminal reactive members provided on the surface of the self assembled structure to covalently bond the drug to be delivered to the surface activated self assembled structure.

In other embodiments, the self assembled structure having an activated surface in accordance with the present disclosure can be attached to biological tissue by functionalizing tissue with one or more reactive members that are complementary to the terminal reactive members provided on the surface of the self assembled structure. Biological tissue can be provided with reactive group that are complementary to the terminal reactive members provided on the surface of the self assembled structure by conjugation of such groups to various components of tissue such as proteins, lipids, oligosaccharides, oligonucleotides, glycans, including glycosaminoglycans. In embodiments, the complementary groups are attached directly to components of the tissue. In other embodiments, the complementary groups are attached to components of the tissue via a linker. In either case, situating the complementary groups on the tissue can be accomplished by suspending the reactive members in a solution or suspension and applying the solution or suspension to the tissue such that the reactive members bind to a target. The solution or suspension may be poured, sprayed or painted onto the tissue, whereupon the reactive members are incorporated into the tissue.

It should, of course, be understood that the self assembled structure having an activated surface in accordance with the present disclosure can be attached to one or more other self assembled structures having a surface activated with complementary terminally located reactive members in accordance with the present disclosure.

The Self Assembled Structure

The self assembled structure described herein are produced by combining of a solvent and a plurality of amphiphilic compounds, each compound including a hydrophobic portion and a hydrophilic portion, the hydrophilic portion functionalized with at least one first reactive member and at least one complementary second reactive member, wherein the first reactive member of at least one of the plurality of amphiphilic compounds is crosslinked with the second reactive member of another of the plurality of amphiphilic compounds.

The solvent and the amphiphilic compound may be combined, mixed or blended, to form the self assembled structures described herein. During self assembly, the hydrophilic portion of the compound will migrate to the outer portions of the self assembled structure while the hydrophobic portions will migrate to the center of the self assembled structure. Because the functionalized hydrophilic portions align with other functionalized hydrophilic portions, the first and second reactive members are positioned in close proximity of one another, thereby allowing them to react and crosslink to form a linkage between the hydrophilic portions of the different amphiphilic compounds. The linkages assist in stabilizing the configuration of the self assembled structures.

Depending on a number of factors, including but not limited to the concentration of the amphiphilic compound, the relative size of the hydrophobic portion compared to the hydrophilic portion and the specific solvent chosen, the self assembled structure may take the form of a spherical micelle or may form a linear micelle or a nanofiber.

The solvent may represent from about 10% to about 99% of the composition by weight, in embodiments, from about 25% to about 95% of the composition by weight.

The amphiphilic compounds may represent from about 15 to about 90% of the composition by weight, in embodiments, from about 5% to about 75% of the composition by weight.

The compositions described herein are intended to self-assemble in physiologic fluids. It is envisioned that the compositions described herein may take the form of a gel-like material or nanofiber.

The compounds, compositions and/or self-assembled structures described herein may be used to make or be incorporated into any medical device suitable for implantation. Some non-limiting examples include monofilaments, multifilaments, surgical meshes, ligatures, sutures, staples, patches, slings, foams, pellicles, films, barriers, stents, catheters, shunts, grafts, coil, inflatable balloon, and the like. The implantable device can be intended for permanent or temporary implantation.

Various modifications and variations of the polymers, amphiphilic compounds, solvents, reactive members, compositions and processes described herein will be apparent to those skilled in the art from the foregoing detailed description. Such modifications and variations are intended to come within the scope of the following claims.

What is claimed is:

1. An amphiphilic compound comprising:
   a hydrophilic portion and a hydrophobic portion, and
   at least a first and second reactive member where the second reactive member is complementary to the first reactive member in that the first and second reactive members are able to interact with one another via a click chemistry reaction to form covalent bonds between each other, said first and second reactive members selected from alkyne groups and azides groups,
   wherein one of said hydrophilic portion and said hydrophobic portion includes both the first and second reactive members.

2. The amphiphilic compound according to claim 1, wherein the first and second reactive members are located on the hydrophilic portion.

3. The amphiphilic compound according to claim 2, wherein the hydrophilic portion includes a plurality of first reactive members.

4. The amphiphilic compound according to claim 3, wherein the hydrophilic portion includes a plurality of second reactive members.

5. An amphiphilic compound according to claim 4, further comprising a terminal reactive member on the hydrophilic portion.

6. The amphiphilic compound of claim 1, wherein the first and second reactive members are located on the hydrophobic portion.

7. The amphiphilic compound according to claim 6, wherein the hydrophobic portion includes a plurality of first reactive members.

8. The amphiphilic compound according to claim 7, wherein the hydrophobic portion includes a plurality of second reactive members.

9. A composition comprising a hydrophilic solvent and a plurality of amphiphilic compounds according to claim 2.

10. A composition comprising a hydrophilic solvent; optionally a catalyst; at least a first amphiphilic compound; and at least a second amphiphilic compound, said first and second amphiphilic compound being an amphiphilic compound according to claim 4.

* * * * *